(12) United States Patent
Griffith

(10) Patent No.: US 7,430,271 B2
(45) Date of Patent: Sep. 30, 2008

(54) RAY TRACING KERNEL

(75) Inventor: Lionell K. Griffith, Solvang, CA (US)

(73) Assignee: Digitome Corporation, Alexandria, VA (US)

( * ) Notice: Subject to any disclaimer, the term of this patent is extended or adjusted under 35 U.S.C. 154(b) by 0 days.

(21) Appl. No.: 10/687,180

(22) Filed: Oct. 15, 2003

(65) Prior Publication Data

US 2004/0114709 A1 Jun. 17, 2004

Related U.S. Application Data

(63) Continuation-in-part of application No. 09/709,586, filed on Nov. 13, 2000, now Pat. No. 6,671,349.

(60) Provisional application No. 60/418,743, filed on Oct. 15, 2002.

(51) Int. Cl.
*A61B 6/00* (2006.01)
(52) U.S. Cl. .......................... 378/24; 378/21
(58) Field of Classification Search .............. 378/4, 378/17, 20–24, 163, 208, 205, 207
See application file for complete search history.

(56) References Cited

U.S. PATENT DOCUMENTS

| 4,472,822 | A | * | 9/1984 | Swift | 378/10 |
|---|---|---|---|---|---|
| 5,051,904 | A | | 9/1991 | Griffith | |
| 5,070,454 | A | | 12/1991 | Griffith | |
| 5,138,642 | A | * | 8/1992 | McCroskey et al. | 378/22 |
| 5,319,550 | A | | 6/1994 | Griffith | |
| 5,371,778 | A | * | 12/1994 | Yanof et al. | 378/4 |
| 6,226,350 | B1 | * | 5/2001 | Hsieh | 378/98 |
| 6,301,325 | B1 | * | 10/2001 | Besson et al. | 378/15 |
| 6,324,246 | B1 | * | 11/2001 | Ruimi | 378/17 |
| 6,400,791 | B1 | * | 6/2002 | Schwarz | 378/15 |
| 6,411,674 | B1 | * | 6/2002 | Oikawa | 378/21 |
| 6,477,221 | B1 | * | 11/2002 | Ning | 378/4 |

FOREIGN PATENT DOCUMENTS

JP 02205760 A * 8/1990

OTHER PUBLICATIONS

Feldkamp et al., "Practical cone-beam algorithm", J. Opt. Soc. Am. A, vol. 1, No. 6, Jun. 1984, pp. 612-619.*
Badea et al., "A 3D Imaging System for Dental Imaging Based on Digital Tomosynthesis and Cone Beam CT", Proceedings Of Medicon 2001, Jun. 12-15, Pula, Croatia.*
International Search Report, dated Oct. 22, 2004.

* cited by examiner

*Primary Examiner*—Chih-Cheng G Kao
(74) *Attorney, Agent, or Firm*—Berliner & Associates

(57) ABSTRACT

A digitized tomosynthesis method, system and apparatus is provided for obtaining 3D volumetric imaging of an object wherein a ray of energy from a source travels through the object to impinge on an energy sensor defining an image plane and the object is rotated about an axis whereby an image is acquired by the energy sensor at successive rotational positions of the object, and wherein the object is rotated about an axis of rotation at a canted angle with respect to the image plane.

42 Claims, 4 Drawing Sheets

US 7,430,271 B2

RAY TRACING KERNEL

CROSS REFERENCE TO RELATED APPLICATION

This application claims the benefit of Provisional Patent Application No. 60/418,743 filed Oct. 15, 2002 and is a continuation-in-part of U.S. patent application Ser. No. 09/709,586 filed on Nov. 13, 2000 now U.S. Pat. No. 6,671,349.

FIELD OF THE INVENTION

The fields of art to which the invention pertains include the fields of dynamic tomography and computed tomography.

BACKGROUND OF THE INVENTION

A unique x-ray imaging and inspection system that combines 3D volumetric imaging and conventional 2D radiography for a complete x-ray inspection solution has been provided under the mark Digitome. For purposes of this application, the system will be referred to a "digitized tomography". Digitized tomography technology has been used for film based 3-dimensional x-ray imaging, and has been enhanced to incorporate digital flat panel x-ray detectors, resulting in examinations being made in minutes. Its features, provide unique capabilities to view any horizontal or vertical plane, scan through the volume in 0.005" increments and measure internal features. See Griffith U.S. Pat. Nos. 5,051,904 ("Computerized Dynamic Tomography System"), 5,070,454 ("Reference Marker Orientation System For A Radiographic Film-Based Computerized Tomography System"), and 5,319,550 ("High Resolution Digital Image Registration"), the disclosures of which are incorporated herein by reference.

The digitized tomography software contains what is known as the digitized tomography kernel. It is a set of software modules that are used to compute digitized tomography views. One defines the geometry by which the images are formed, the data arrays that contain the image data, and the coordinates of an object space. The resultant voxel value is returned to the calling software. It is the calling software's responsibility to resend the coordinates and store the voxel values so they produce the desired digitized tomography view foil.

From its inception, the digitized tomography kernel was based upon a digital simulation of what is known as the film mode. Referring to FIG. 1, its geometric derivation assumes the source 10 is at a canted angle with respect to the image plane 12. The object to examine is positioned centrally over the intersect 14 of the x-ray source optical axis 16 and the image plane. The object is then is stepwise rotated about an axis perpendicular to the image plane 12 and that passes through the above intersect. An x-ray image is acquired at each rotation position of the object.

In the film simulation mode, each acquired image is rotated by the same angle as was the object when it was exposed. The resulting images are stacked with their axes of rotation coincident. Finally, each image is translated radially outward from the axes of rotation by a distance related to the object level one desires to observe. The translation distance is a function of the perpendicular distance between the image plane and the view plane. Light passing through a stack of film positioned thusly will reveal the features at the desired view plane.

Referring to FIG. 2, an alternate geometry would be useful. For example, the x-ray optical axis 16 could be perpendicular to the image plane and the axis of rotation of the object could be at another angle with respect to the image plane 12. This would allow the instrumentation to fit into a much smaller column because the source is immediately above the image plate rather than offset to the side. It would also permit larger and taller objects to be examined using a given image plate than does the current geometry.

BRIEF SUMMARY OF THE INVENTION

The present invention is directed to a digitized tomography method, apparatus and kernel that can also include the currently used geometry, the alternate geometry, and potentially many other geometries. In an alternate geometry for operation of the digitized tomography kernel, the x-ray optical axis is perpendicular to the image plane and the axis of rotation of the object is at a canted angle with respect to the image plane. A film mode simulation geometry is provided wherein the object plane is not parallel to the film plane and the geometric magnification varies over the film plane. Methods are provided by which a marker disk and misalignment post are placed to calibrate the alternate geometry.

More particularly, a digitized tomosynthesis method, system and apparatus is provided for obtaining 3D volumetric imaging of an object in which a ray of energy from a source travels through the object to impinge on an energy sensor defining an image plane and in which the object is rotated about an axis whereby an image is acquired by the energy sensor at successive rotational positions of the object, and wherein, in accordance with the invention, the object is rotated about an axis of rotation at a canted angle with respect to the image plane. In specific embodiments, the energy is in the form of electromagnetic radiation, particularly x-ray radiation, and the energy sensor is a flat panel digital detector. A ray of energy from the source is mathematically traced through a voxel of the object space to the image plane, the coordinate of the shadow of the voxel on the image plane is computed for each object rotation, and the image data is extracted and combined to form the object space voxel. In preferred embodiments, the optical axis of the source is perpendicular to the image plane, but other geometries are useful.

The source and object angles relative to the energy sensor are determined by: determining the axis of rotation of the object; placing a first registration marker that is substantially opaque to the energy on a first location proximate the sensor and along the object's axis of rotation; obtaining a first shadow image corresponding to the first registration marker by exposing the first registration marker to energy from the energy source; placing a second registration marker that is substantially opaque to energy levels at a location distal from the sensor, spaced a predetermined distance from said first location along the object's axis of rotation; obtaining a second shadow image corresponding to the second registration marker by exposing the second registration marker to energy from the energy source; and comparing a location of the first shadow image and a location of the second shadow image to determine the source and object angles relative to the energy sensor.

The first registration marker and the second registration marker can be the same marker, the second registration marker being supported at the predetermined distance by a pedestal that is substantially transparent to said ray of energy.

The orientation between the energy source and the sensor surface includes at least one of, preferably both of, an angle of misalignment and an angle of inclination of the rotational axis of the object. The object is positioned proximate the surface of the energy sensor, a shadow image with the energy sensor is obtained by exposing the object to energy from the energy source, and the shadow image is manipulated as a function of the orientation between the energy source and the sensor surface. The energy source and/or the object, preferably the object, is rotated about a center of rotation to a plurality of rotational positions; obtaining an object shadow image at each of the plurality of rotational positions. The object shadow images obtained at the plurality of rotational positions are combined to obtain a three-dimensional image of the object; which is manipulated as a function of the orientation between the energy source, the rotational axis of the object, and the sensor surface.

Features and advantages of the invention will be described hereinafter which form the subject of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

DETAILED DESCRIPTION OF THE INVENTION

A computed combination of the data from a series of digitally acquired images will result in the same view obtained in the previously referred to film simulation mode and requires the combination of registered pixels from each of the digitized images. The method is described in Appendix A. In addition, other view foils are possible to compute simply by changing the pattern of the voxel coordinates passed to the digitized tomography kernel as well as various image enhancements. The film mode simulation digitized tomography kernel math is described in Appendix B wherein the kernel is limited to the axis of rotation of the object being perpendicular to the image plane.

Math Model

Figure 3:
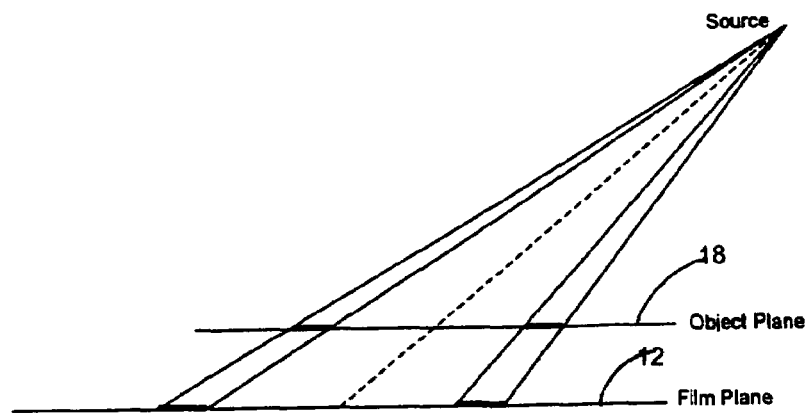
FIG. 3 is a schematic representation of a film mode simulation geometry wherein the object plane is parallel to the film plane and the geometric magnification projects uniform shadows of the features of the object plane.

The film mode simulation geometry works in the film mode because the object plane is parallel to the film plane. Referring to FIG. 3, the geometry is such that the geometric magnification of projected shadows of the features of the object plane 18 is uniform. Thus the appropriate superposition of the film images places the projected shadows of the features of the view image plane in coincidence.

Figure 4:
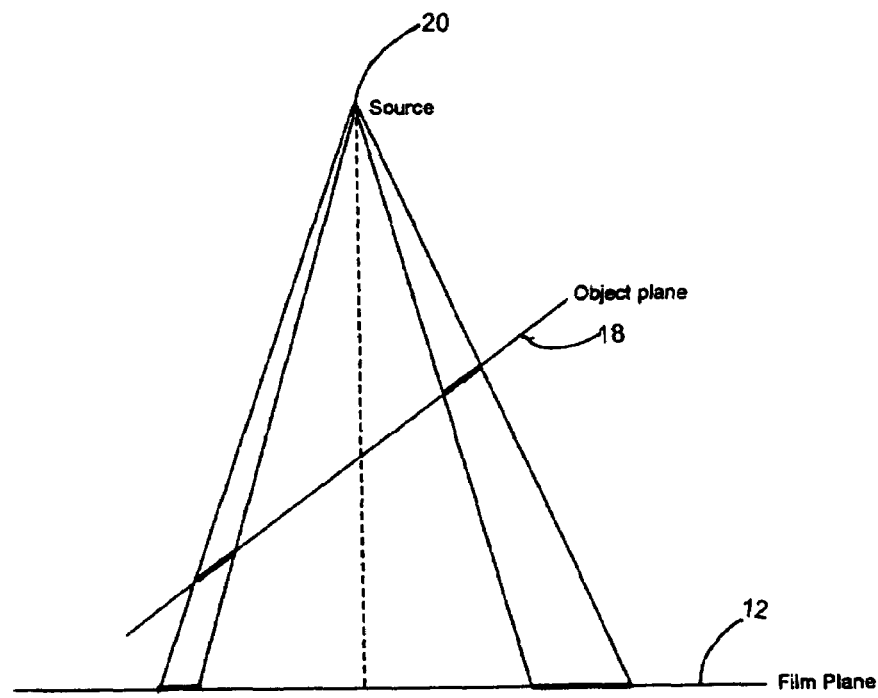
FIG. 4 is a schematic representation of an alternative geometry wherein the object plane is not parallel to the film plane and the geometric magnification varies over the film plane.

Referring to FIG. 4, in the alternate geometry, the object plane 18 is not parallel to the film plane and thus the geometric magnification varies over the film plane. Since the film is dimensionally fixed, it is therefore not possible to superposition the film so that the projected shadows of the features of the object plane are in coincidence. In order to form an image by combining alternate geometry projections, one must accommodate the variation of magnification.

If one specifies the geometry of image formation sufficiently, one can mathematically trace a ray from the source 20, through the object space voxel to the image plane and compute the coordinate of the shadow of the voxel on the image plane. If done for each object rotation, the image data could be extracted and combined to form the estimate of the given object space voxel. Since the ray tracing process includes the geometric magnification effects, both the current and alternate geometries are applicable, as are many other geometries. The geometry can be specified with sufficient accuracy and precision to achieve acceptable results.

Limits to Resolution

There are three primary factors limiting resolution.

The first limitation is the spot size of the x-ray source 20. Each edge of the projected image has a penumbra caused by that spot size. Its dimension is the spot size times the distance between the object feature and the image plane divided by the distance between source 20 and the image plane. Since the usual spot size is in the order of a millimeter, the source distance in the order of a meter, and the feature distance is in the order of a few tens of millimeters, the penumbra is in the order of a few tens of thousandths of a millimeter or a few thousandths of an inch. The alternate geometry may have larger penumbra due to the larger distances between the object feature and the image plane. Using a smaller spot size and/or longer source distances can reduce this effect.

The second limitation is the pixel size of the image plate. Since we use data from eight or more images, its possible to obtain resolutions better than the pixel size of the image plate. Use of multiple images also tends to cancel a portion of the penumbra effect.

The third limitation is the specification of the geometry. Errors in the specification of the position of the source 20 have an effect similar in magnitude as the penumbra effect. Those errors are attenuated by the ratio of the source distance to feature distance. Errors in the identification of the center of rotation has a one to one impact. Errors in specification of the various angles are dependent upon the distance over which the error is communicated. Acceptable errors for the current image plate are in the order of a few hundredths of a degree.

With such tight tolerance of angles and dimensions, the geometry must be either very carefully measured or calibrated by using the system and specially constructed objects.

Specifying the Geometry

Figure 1:
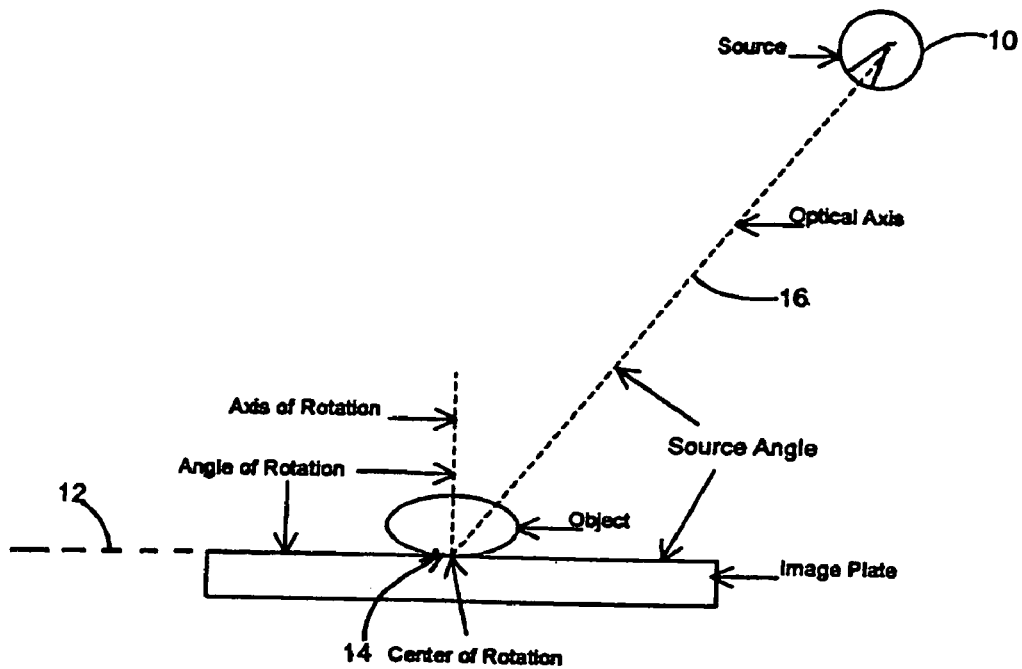
FIG. 1 is a schematic depiction of film mode operation of the digitized tomography kernel wherein the source is at a canted angle with respect to the image plane.
Figure 2:
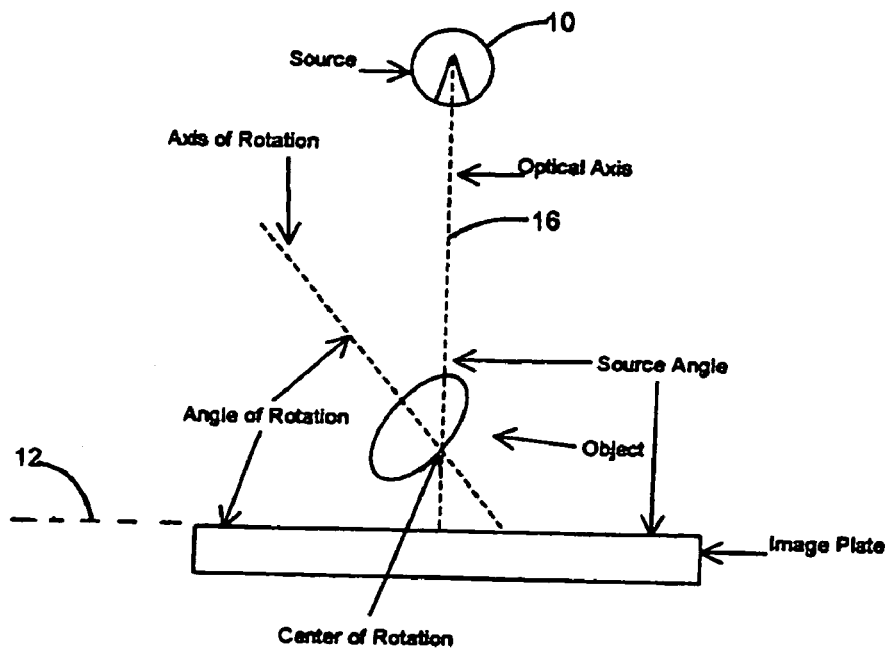
FIG. 2 is a schematic depiction of an alternate geometry for operation of the digitized tomography kernel wherein the x-ray optical axis is perpendicular to the image plane and the axis of rotation of the object is at a canted angle with respect to the image plane.

The assumption is that there is a fixed relationship between the source 20 and image plate, that the object is between the source 20 and the image plate, and that it is the object that is rotated about a fixed axes between each exposure cycle. This restriction can be removed by measuring the precise location and orientation of the source 20, the object, and image plate. However, since the goal is to achieve a working system within the bounds of currently available technology, the above restrictions are necessary. Relatively simple input transformations can be used, if required, to adapt to precise and accurate location and orientation measurements The Coordinate System Looking at the system as it is presented in FIGS. 1 and 2, the X axis is left to right, the Y axis is vertical, and the Z axis is in and out. The origin of the system is the outer left most pixel on the image plate. One coordinate increment is equal to one pixel. This makes the image plate coincident with the X,Z plane. The X,Z plane in the new coordinate system is the same as the X,Y plane of the original system. The change is necessitated by the three dimensional (3D) math required by the alternate geometries. The original geometry only required two dimensional (2D) math.

Dimensions to Specify
1. The source to image plate distance (Source Distance)
2. The image plate dimensions (Width in Z axis, Height in X axis)
3. The image plate pixel size (From vendor)
4. The center of rotation to image plate distance (Object Distance)
5. The object radius of interest (From operator)

The source to image plate distance is not critical. Errors are diminished by the ratio of the feature to image plate distance to the source to image plate distance.

The image plate dimensions and pixel size are given by the manufacturer.

The center of rotation to image plate distance is also not critical. Its used to compute the object plane level offset so that one can specify the view level as distance from the base of the object.

The object radius of interest is perhaps the least critical. It simply sets the computed image size. It is necessary that it is sufficient to include the features of interest but not so large as to unnecessarily extent the computation time.

Angles to Specify
1. The source to image plate plane angle in the YZ and XZ planes (Source Angle)
2. The object axis of rotation to image plate plane angle in the YZ and XZ planes (Object Angle)
3. Rotation angle of object for each image (Rotation Angle)

In accordance with this invention, one defines, by manufacture and/or by measuring the source to image plate plane angles and the object axes 'of rotation to image plate plane angle as closely as reasonably possible. Small errors can be measured using the system and specially constructed objects and corrections can be computed. If the manufacture or measurement is precise and accurate enough, corrections won't be required, in which case the ray tracing method is not limited to any particular geometries.

It is apparent from our current system that the manufacture of the means to set the rotation angle of the object is sufficiently precise and accurate for the existing image plate.

Calibrating the Geometry

Figure 5:
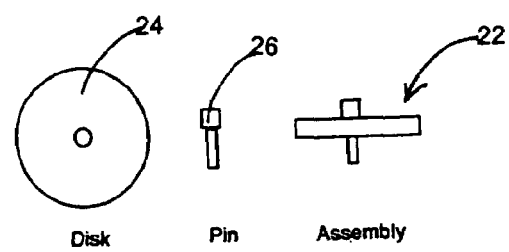
FIG. 5 depicts a marker in the existing system in which the object is a round marker disk with a central pin made of a material suitably opaque to x-rays.

The existing system uses a two step geometry calibration. Referring to FIG. 5, the object 22 is a round marker disk 24 with a central pin 26 made of a material suitably opaque to x-rays.

Figure 6:
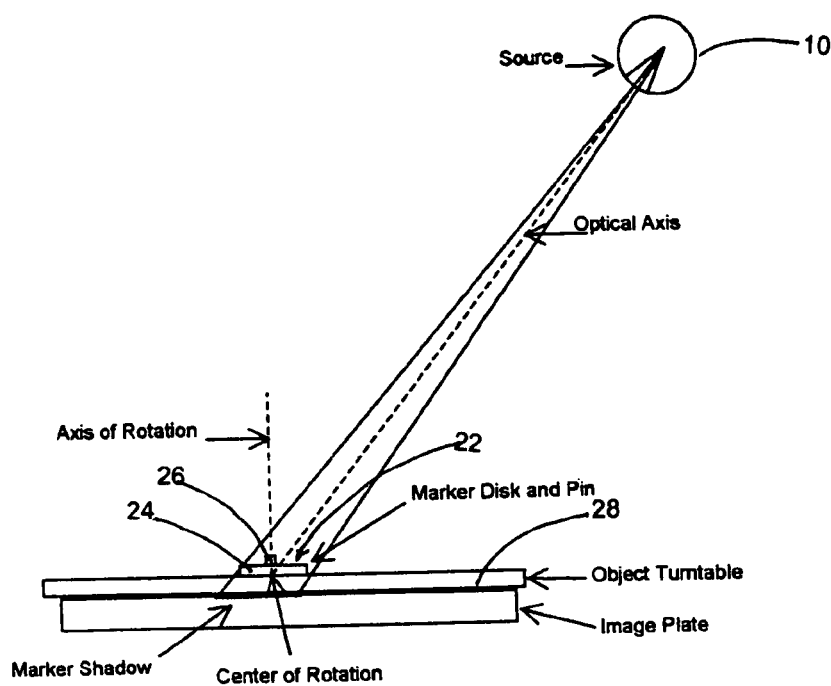
FIG. 6 depicts use of the disk and pin of FIG. 5 in a first step in calibrating the geometry of the system.
Figure 7:
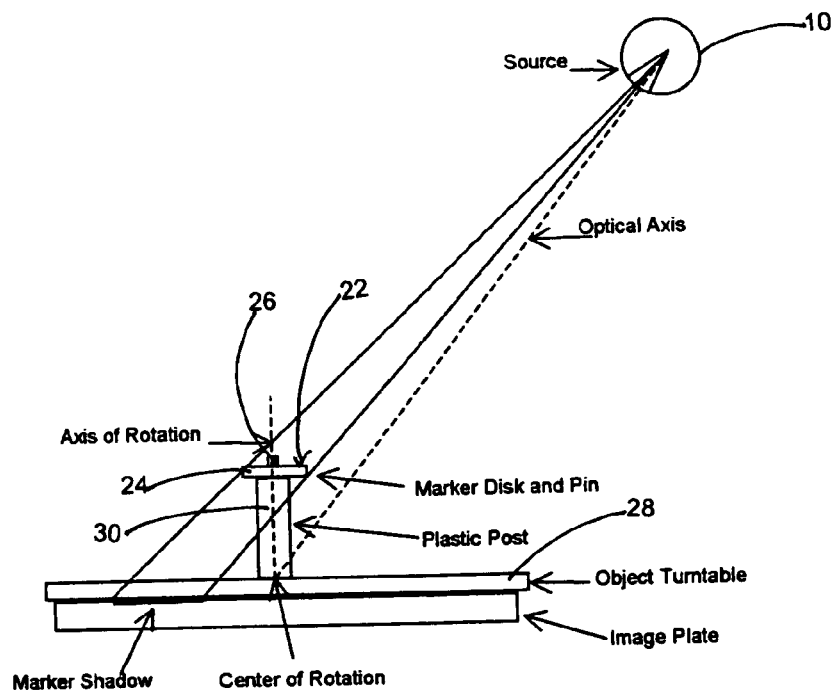
FIG. 7 depicts a plastic post with a similar pin at one end and hole to receive the pin of the round disk, inserted into the central hole of the object turntable in a second step in calibrating the geometry of the system.

Referring to FIG. 6, in the first step, the disk 24 is retained on the object turntable 28 via insertion of the bottom of the pin 26 through the disk 24 and into a hole in the center of the object turntable 28. An image is taken and is used to discover the coordinates of the center of rotation. In the alternate geometry, it is used in the same manner Referring to FIG. 7, in the second step, a plastic post 30 carries the marker disk and pin assembly at its top end. The plastic post 30 has a similar pin at its bottom end, inserted into the central hole of the object turntable 28, and a hole at its upper end to receive the bottom of the pin 26 through the round disk 24. A second image is taken and is used to discover the misalignment coordinate. The central coordinate of the marker shadows is measured by the graphical interactive method, described in Appendix C.

Figure 8:
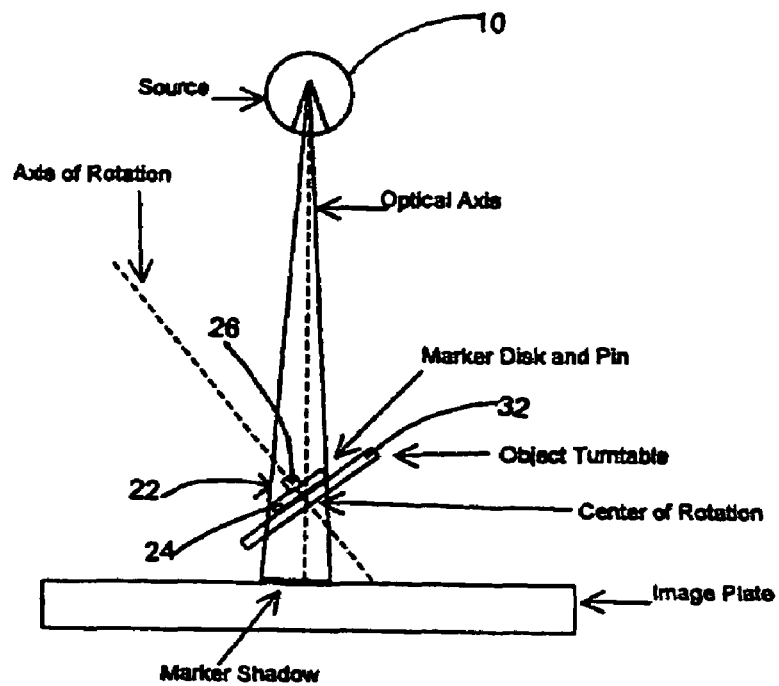
FIG. 8 depicts one method by which the marker disk and misalignment post are placed to calibrate the alternate geometry.
Figure 9:
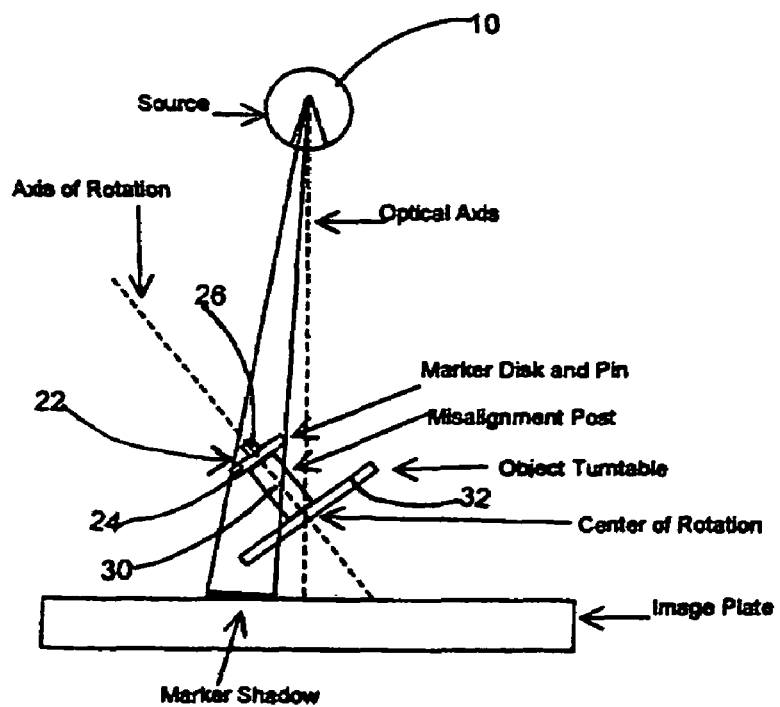
FIG. 9 depicts another method by which the marker disk and misalignment post are placed to calibrate the alternate geometry.

The center coordinate, the misalignment coordinate, the length of the plastic post 30, and the pixel size are used to compute corrections for the source and object angles. This calibration technique is the subject of my U.S. patent application Ser. No. 09/709,586, filed Nov. 13, 2000, entitled "Tomosynthesis System and Registration Method," hereby incorporated herein by reference. However, it was not then extended to the alternate geometry. FIGS. 8 and 9 indicate how the marker disk 24 and misalignment post can be placed on an angled object turntable 32 to calibrate the alternate geometry.

Axial Misalignment Calibration

The digitized tomography process requires very precise image registration for it to produce high quality computed images. The requirement is such that every pixel in every source image must be known to the process to within a fraction of a pixel. A method that provides for such high resolution image registration of film x-ray images consists of a fixture, a setup process, and calibration procedure that assures a very specific geometry of exposure and allows each digitized film image to be transformed into a standard registration and format. Because the x-ray source is position immediately overhead the center of rotation of the fixture and the fixture is tilted to the desired angle that axial misalignment of the x-ray images is not encountered.

The current digitized tomography calculations assume the path between the center of the x-ray source and the center of rotation of the non-film fixture's turntable 28 falls on a plane that is perpendicular to the non-film image plate's surface, parallel to the long axis (the "Y" axis) of the non-film image plate, and passes through the center of rotation of the fixture's turntable 28. Since the current fixture is placed horizontally and the x-ray source is moved to the side and angled toward the center of rotation, an axial misalignment is possible without using special alignment procedures and tools. Even a small misalignment can cause serious degradation of the resultant computed digitized tomography views.

Currently, the center of rotation is calibrated using an image of a circular marker placed at the center of rotation in a manner identical to the method used to identify the center of rotation of film images. Because all images can be taken with an identical registration, the three reference mark technique used with film images is not required. However, a second reference mark must be used to measure the axial misalignment of the x-ray optical axis. That marker may be of the same size and material as the center reverence mark but must be displace above the center of rotation by some distance. Since the center position of the marker can be determined to approximately ½ a pixel width, that distance need only be approximately ½ the maximum possible image radius. The current image plate is 2304 pixels wide with a 200 pixel "gutter" along one edge. That makes the effective radius (2304−200)/2=1145 pixels at 0.005 inches per pixel, that is, 5.724 inches. One half of that is 2.86 inches.

Using the center coordinates of the two reference markers, the axial misalignment angle can be determined and a correction to the digitized tomography calculations can be applied to the "X" and "Y" axis displacement values. The process is as follows:

Let x1,y1 be the pixel coordinate of the center of the center reference mark image. Let x2,y2 be the pixel coordinate of the center of the elevated center reference mark image. Let the x-ray optical axis be more or less parallel to the "Y" axis in the positive direction. The distance between centers of the reference marks is computed by taking the square root of the sum of the squares of the differences between the first and second coordinates: distance=sqrt((x1−x2)*(x1−x2)+(y1−y2)"(y1−y2)). That distance is divided into the differences between the coordinates to compute the sine and cosine of the misalignment angle: sine of misalignment angle=(x2−x1)/distance and cosine of misalignment angle=(y2−y1)/distance.

The Displacement is the normally calculated displacement value and is computed as a function of the image level. The "X" axis displacement value is computed as the Displacement times the sine of the misalignment angle and the "Y" axis displacement value is computed as the Displacement times the cosine of the misalignment angle. The adjusted displacements are applied to their respective axis calculations as described elsewhere. A procedure similar to the one used with the film mode simulation geometry can be used to compute and apply the corrections to the alternate geometry.

An additional calibration step can be applied to the alternate geometry—the distance between the image plate and the center of rotation (object distance). Errors in that dimension can affect the accuracy of measurement of feature size, although simple measurement should be enough because the effect of that error is the size of error divided by the source distance. One way to calibrate that dimension is to place two marker disk 24 and pin 26 assemblies a known distance apart on the object turntable 32, centered on the center of the turntable 32 and oriented so the line connecting the centers of the disks is parallel to the Z axes. The following relationship are true:

Solving for the object distance gives a calibrated estimate of the required dimension.

Ray Tracing Process
1. Compute alignment calibration angles
   a. Acquire centroid of center calibration marker shadow in image plane
      i. Coordinate is X1a,Z1a by method in Appendix C
      ii. Note: the image plane is parallel with the XZ plane
      iii. Note: the origin of the image plane is at the coordinate system origin
   b. Acquire centroid of misalignment calibration marker shadow in image plane
      i. Coordinate is X1b,Z1b by method in Appendix C
      ii. Note: if Z1a equals Z1b there is no misalignment
   c. Compute misalignment angle in XZ plane
      i. Misalignment angle equals arctan((X1b−X1a)/(z1b−z1a))−90°
   d. Compute angle in XY plane
      i. Convert height of misalignment calibration post to pixel units
      ii. Source angle equals arctan((misalignment post height)/(X1b−X1a))
      iii. For current geometry, angle is source angle
         1. Object angle is 0°
         2. Presumes accurate construction
         3. Implies object plane is parallel to image plane
         4. Construction and calibration procedure seems adequate
      iv. For alternate geometry, angle is object angle
         1. Source angle is 90°
         2. Presumes accurate alignment of image plane to source path
         3. Implies optical axis is normal to image plane
2. Compute corrected 3D coordinates of source
   a. Transform source distance to pixel units
   b. Xs=X1a
   c. Ys=(source distance)×sin(source angle)
   d. Zs=Z1a
3. Compute equation of image plate plane
   a. Vector 1=(0,0,0),(0,(image width −1),0)
      i. Vx1=0
      ii. Vy1=image width −1
      iii. Vz1=0
      iv. M1=sqrt(Vx1^2+Vy1^2+Vz1^2)
   b. Vector 2=(0,0.0),(0,(image height −1),0)
      i. Vx2=0
      ii. Vy2=image height −1
      iii. Vz2=0
      iv. MZ=sqrt(Vx2^2+Vy2^2+Vz2^2)
   c. Normal Vector=the normalized cross product of Vector 1 and Vector 2
      i. Non-normalized vector
         1. NVx=(Vy1×Vx2)−(Vx1×Vy2)
         2. NVy=(Vz1×Vx2)−(Vx1×Vz2)
         3. NVz=(Vx1×Vy2)−(Vy1×Vx2)
         4. NM=sqrt(NVx^2+NVy^2+NVz^2)
      ii. Normalized vector
         1. NVx=NVx/NM
         2. NVy=NVy/NM
         3. NVz=NVz/NM
   d. Plane coefficient
      i. D=−NVx×Vx1−Nvy×Vy1−NVz×Vz1
4. For each object voxel in desired digitized tomography view foil
   a. Compute 3D coordinates of object voxel
      i. Transform engineering units coordinate to pixel unit coordinate
      ii. Two dimensional coordinate transformations in XZ plane
         1. Rotate about axis of rotation to misalignment angle
         2. Rotate about axis of rotation to incremental angle
      iii. For alternate geometry
         1. Two dimensional coordinate transformation in XY plane
            a. Rotate about center of rotation to object angle
            b. Translate to the center of rotation
   b. Use results of 1 and 4a to create a 3D line
      i. (Xs,Ys,Zs),(Xo,Yo,Zo)

c. Use results of 3 and 4b to compute intercept coordinates
  i. Dx=Xo−Xs;
  ii. Dy=Yo−Ys;
  iii. Dz=Zo−Zs;
  IV. mu=−(D+NVx×Xd+Nvy×Yd+NVz*Zd)/(NVx×Dx+Nvy×Dy+NVz×Dz)
  v. Xi=Xs+mu×Dx
  vi. Yi=Ys+mu×Dy
  vii. Zi=Zs+mu×Dz
d. For each image
  i. Use results of 4c to extract projected ray pixel value
    1. Method in Appendix B
e. Combine pixel values from 4d by method in Appendix A
f. Store result of 4e in destination digitized tomography view data matrix.

APPENDIX A—VARIABLE ABSORPTION DIGITAL IMAGE COMBINATION

Review of Absorption Digital Image Combination:

The process of producing a Computed Tomographic View from multiple digitized x-ray images requires the combination of the registered pixels from each of the digitized images. The usual method used is a simple summation or averaging of the pixels to be combined. This method results in an image containing many confusing artifacts and visual blurring.

The original absorption model for combining eight images is as follows:

The minimum pixel value was assigned a transmission fraction of 0.5

The maximum pixel value was assigned a transmission fraction of 1.0

All other pixel values were assigned a transmission fraction proportionately between 0.5 and 1.0

For each pixel location in the computed view

Start with a maximum pixel value

Successively multiply initial pixel value by the transmission fraction of that same pixel location in each of the eight images This can be accomplished using integer arithmetic as follows:

Combined pixel=Maximum pixel value
For each of eight images in succession
  Image pixel=Image pixel+Maximum pixel value
  Image pixel=Image pixel DIV 2
  Image pixel=Image pixel−Maximum pixel value
  Image pixel=Image pixel*Combined pixel
  Image pixel=Image pixel DIV Maximum pixel value
  Combined pixel=Combined pixel+Image pixel
Note: While floating point arithmetic could be used, integer arithmetic is much faster on most computers
Note: While eight images were used in the present case, the method could be adapted to other numbers of images Variable Absorption Digital Image Combination:

While the fixed absorption model gave generally good results, it was thought that other values of absorption might give improved results for some examinations. For example, examinations of very dense objects might benefit from higher absorptions while examinations with low density areas of interest might benefit from lower absorptions.

The fixed absorption model has been modified to allow variable absorption using integer arithmetic as follows:

Combined pixel=Maximum pixel value
For each of eight images in succession
  Image pixel=−Image pixel+Maximum pixel value
  Image pixel=Image pixel DIV 2
  Image pixel=Image pixel−Maximum pixel value
  Image pixel=Image pixel*Combined pixel
  Image pixel=Image pixel DIV Maximum pixel value
  Image pixel=Image pixel*Scaled absorption fraction
  Image pixel=Image pixel DIV Scaling factor
  Combined pixel=Combined pixel+Image pixel
Note: While floating point arithmetic could be used, integer arithmetic is much faster on most computers
Note: While eight images were used in the present case, the method could be adapted to other numbers of images If the absorption fraction is one, the results are as before. Given an absorption fraction greater than one, the effect is to increase the absorption. While, an absorption fraction less than one results in a decrease of absorption effect. Visual results are as expected.

APPENDIX B—HIGH RESOLUTION DIGITAL IMAGE MANIPULATION

Review of Between Pixel Value Calculation:

A digitized image is a rectilinear matrix of numbers. Each number represents the integral intensity of a small area of the original object, picture, or transparency. In order to transform the matrix to an image the eye can use, hardware must be provided such that each number can be presented as a small area of light or dark on a video display or printing device.

When the eye looks at a small area of light, a perception of brightness results from an integration of area and intensity. That is a small area of bright will look as bright as a slightly larger area of slightly less brightness. This understanding lead to the following method of determining the value of a pixel whose coordinate fell between pixels.

Given:
  A two dimensional matrix of pixel values for a source image
  A fractional coordinate of a pixel value to determine
  coordinate=x.fx,y.fy
  Where:
    x,y=the integral coordinate
    fx=the fractional x coordinate
    fy=the fractional y coordinate There are four nearest pixels in the source image
  Upper left=x,y
  Upper right=x+1,y
  Lower left=x,y+1
  Lower right=x+1,y+1

There are four areas joining at x.fx,y.fy which are proportional to
  =>Upper left=fx*fy*Aspect ratio
  =>Upper right=(1−fx)*fy*Aspect ratio
  =>Lower left=fx*(1−fy*Aspect ratio)
  =>Lower right=(1−fx)*(1−fy*Aspect ratio)
  Where:
  Aspect ratio=y pixel resolution/x pixel resolution
  It was concluded that the eye will weight the four nearest pixels proportional to the opposing areas Between pixel value = (Upper left value * Lower right area +

Upper right value * Lower left area +

Lower left value * Upper right area +

Lower right value * Upper left area) / Aspect ratio

Applications of between pixel value calculation:
  The between pixel value calculation is currently used for two applications in the DT33 and DT36 programs:
    Rotation and translation of digitized images
    Forming the measure feature profile line
  Tests have been performed yielding very good results for two more applications:
    Digitized image magnification
    Extended high resolution reference mark find
  Several additional applications should be quite possible but are as yet untested:
    Variable image area selection
    Calculation of arbitrary z-axis view
    Correction of digital image distortion
      Magnification
      Aspect ratio
      Non-linear distortion Review of Rotation and Translation of Digitized Images:

The digitized images must be rotated and translated for two reasons:
1 The acquired image must be rotated and translated to a standard reference rotation and position
2 The set of images for an examination must be rotated and translated so that the image combination will yield the computerized tomographic view at the desired level Given:
  A two dimensional matrix of pixel values for a source image
  A two dimensional matrix of pixel value locations for a destination image
  A coordinate of the image center of rotation
  A reference coordinate for the image center of rotation
  An angle to rotate about the image center of rotation
  An x displacement of the image center of rotation
  An y displacement of the image center of rotation Transform each integral coordinate in the destination image into a fractional coordinate in the source image:

$$x.fx = (x \text{ destination} - \text{source center } x - x \text{ displacement}) *$$
$$\text{COS(rotation angle)} +$$
$$(y \text{ destination} - \text{source center } y + y \text{ displacement}) *$$
$$\text{SIN(rotation angle)} -$$
$$(2.0 * \text{source center } x - \text{reference } x)$$

$$y.fy = (x \text{ destination} - \text{source center } x - x \text{ displacement}) *$$
$$\text{SIN(rotation angle)} +$$
$$(y \text{ destination} - \text{source center } y + y \text{ displacement}) *$$
$$\text{COS(rotation angle)} +$$
$$(2.0 * \text{source center } y - \text{reference } y)$$

Compute the between pixel value in the source image at x.fx,y.fy and place it in the destination pixel location x destination,y destination.

Review of Forming the Measure Feature Profile Line:

The operator selects two points on the image which are the ends of a line passing through the feature of interest.

Given the coordinates of the two points x1,y1 and x2, y2

Compute the slope of the given line:
  IF x1<>x2 THEN slope=(y2−y1)/(x2−x1)
  ELSE slope=sign of (y2−y1) 1E20 or similar large number Compute the intercept of the given line:
  intercept=y1−slope*x1

For each one pixel distance between the two points on the line compute the fractional coordinate:
  Compute:
  x increment=SQRT (1/(1+SQR(slope)))
  y increment=slope*x increment
  x.fx=x1+x increment*number of pixels from x1, y1
  y.fy=y1+y increment*number of pixels from x1,y1

For each fractional coordinate compute the between pixel value to be the corresponding feature profile line pixel value.

Digitized Image Magnification:
  Previous applications were based upon the fractional coordinates being one image pixel apart. If the fractional coordinates are spaced closer than one pixel apart the destination image is effectively magnified. That is if they are ½ pixel apart the effective magnification is 2×; ¼ pixel apart is 4× and so on.
  When such a magnification is done the result is a smooth magnification of the digitized image-that appears much like the image produced by a magnifying glass. The customary approach to the magnification of a digital image is the simple square replication of each pixel. That is for a 2× magnification each pixel is replicated into a 2 by 2 square. The resulting image appears magnified but has a square tile effect which reduces the eyes ability to see the shape of the magnified features.
  Magnification of digital images is becoming more important as the resolution of image digitizers and digital display devices improves. Current resolution is such that it is difficult to see features that are a few pixels in size. This trend is expected to continue.

Extended High Resolution Reference Mark Find:
  The current method of locating the center of the registration reference marks is as follows:
    The operator points to the inside of the reference mark
    The computer scans on the x and y axis until it finds a maximum in the slope of the image intensity higher than the noise peaks
    The fractional coordinates of the maximum slope is determined
    The position of the maximum is determined by using the maximum slope along with the preceding and following slope values to form a second order curve
    The position of the maxima of the second order curve is assumed to be the position of the edge
    The trial center of the mark is then computed as the mean x,y coordinate
    The computer then takes the trial center and similarly computes a second trial center
    The compute then takes the second trial center and computes the final center coordinate
  Since the reference marks are ellipsoidal:
    The center coordinate of both reference marks are determined
    The errors in angle and position are computed The rotation and position of the image is adjusted by the rotation and translation procedure The computer then determines the new center coordinates of the reference marks The sequence is repeated until the errors in angle and position are reduced below a small amount An extended method is as follows:

The operator points to the inside of the reference mark

The computer scans on the x and y axis until it finds a maximum in the slope of the image intensity higher than the noise peaks The fractional coordinates of the maximum slope is determined The position of the maximum is determined by using the maximum slope along with the preceding and following slope values to form a second order curve The position of the maxima of the second order curve is assumed to be the position of the edge The trial center of the mark is then computed as the mean x,y coordinate The computer then takes the trial center and similarly computes a second trial center The compute then takes the second trial center and computes the final center coordinate Do the above for both reference marks Compute the angle and positional error Use the same method used to create a feature profile line to produce an x,y scan across the reference marks whose angle is adjusted for the angular error found above In a similar manner find the fractional coordinates of the maximum slope in the pixel intensity Compute the center coordinates for both reference marks as the mean coordinate of each Compute a revised angle and position error Repeat the second process until the computed angle and position error changes less than some small amount The advantage of this extended method is that the true error in angle and position of the image is determined without the time consuming multiple rotation and translation adjustment. This becomes vary important as the resolution of the digitized image improves. Current images are 3.1 meg pixels with a possible 12.6 meg pixels soon. The higher resolution image will take too much time and memory to allow such adjustment.

Variable Image Area Selection:

The current method of image area selection is as follows:

The image is adjusted to standard position and rotation

The operator selects a packing fraction 1 to 1 4 to 1 9 to 1 16 to 1

The central area of the source image is packed into the destination image area

This method has several problems:

The time and memory required to adjust the digitized image to standard position and rotation The inflexibility of the integral pixel packing approach not allowing optimum sizing of the area of interest after digitization Demagnification of the digitized image should be possible in a manner vary similar to the magnification discussed above. Compute the fractional coordinates so that they are more than a source pixel apart. Any arbitrary demagnification should be able to be achieved.

Rotation and translation can be accomplished at the same time by using the extended reference mark find method coupled with the coordinate transformation procedure above. Thus the excessive time and memory required for the current method can be eliminated along with allowing an optimum selection of the area of interest.

Calculation of Arbitrary z-Axis View:

The current method of computation of a z-axis view is limited to any x or y line in the currently formed computed tomography view series. A specific x or y line is taken from each stored computed tomographic view and displayed side by side. This is not quite satisfactory because:

The entire series must be created first

Too much time is taken read all of the data from the disk

The feature of interest may not be along the x or y axis

The feature of interest may in fact be curved

An alternative is:

The operator selects an arbitrary path on one view

A list of fractional coordinates one pixel apart are generated from that path or possibly magnified or demagnified as required Transform that list so that the appropriate rotations and translations are included Acquire pixel data along that transformed path by the above between pixel method Combine the pixels by the currently used absorption method Present the computed paths side by side Correction of Digital Image Distortion:

If an array of fractional coordinates can be computed to correct for the distortion in a digital image, the above between pixel calculation can be used to correct that distortion. Thus linear distortion such as magnification or aspect ratio can be corrected with ease. Non-linear distortion such as that resulting from a variable speed scanning camera can be corrected if that non-linearity were adequately known.

APPENDIX C —HIGH RESOLUTION REGISTRATION OF DIGITAL IMAGES

The coordinate system to be used in this disclosure is as follows:

The film is placed at the image plane

The image plane is the x,y plane

The image plane is tilted at some angle with respect to a base plane

The y axis is parallel to be base plane

The image is formed by x-rays projecting a shadow of an object at or near the image plane Multiple images are formed by rotating the object about an axis of rotation The z axis is parallel to the axis of rotation The intersect of the axis of rotation and the image plane is the center of rotation The center of rotation is the desired origin of the coordinate system Previous disclosures described a method of using reference marks to transfer the registration of the object to the computer. Several methods of locating and using the centers of those markers were discussed.

As the image resolution is pushed to higher levels, registration becomes a more demanding problem to be solved. For digitized tomography brand Computerized Tomography to work at its best, the multiple digitized images must be in registration to within a pixel.

After digitization of the x-ray images, the two registration marks centers are located, the apparent center of rotation is computed based upon a previously established relationship between the registrations marks and the center of rotation. The image is then moved to a standard position and rotation:

The line joining the centers of the registration marks is parallel to the y axis The center of rotation is positioned at the center of the digital image Since the acquired images must be rotated to form the final CT view, the quality of the result is vary sensitive to variations in registration along the y axis. This is especially true as the area of interest is more distant from the center of rotation.

When working with pixels as small as a few mills, the projected image of the reference marks becomes an ellipse rather than a circle. Center find routines based upon the assumption of a circle fail to locate the center of the mark to within the required fraction of a pixel. In fact, variations in the position of the final image of more than five pixels, have been observed.

Methods have been developed that markedly reduces this problem.

Review of Previously Disclosed Center Find Methods:

First Attempt—No Longer in Use:

Step Description
1 Locate the coordinates of all reference mark edge pixels
2 Compute mean x and y coordinate
3 Use computed x,y coordinate as center of reference mark Method One—In Use:

Step Description
1 Use mouse to point to inside of reference mark
2 Use pointed to pixel as starting point
3 Scan along the x axis to find maxima or minima of differential of pixel level
4 Compute x coordinate of left and right edge of reference mark as position of maxima or minima of differential
5 Compute mean x coordinate
6 Scan along the y axis to find maxima or minima of differential of pixel level
7 Compute y coordinate of top and bottom edge of reference mark as position of maxima or minima of differential
8 Compute mean y coordinate
9 Use computed mean x,y coordinate as center of reference mark Method two—in use:

Step Description
1 Use mouse to point to inside of reference mark
2 Use mouse to point to outside of reference mark
3 Use pointed to inside pixel as starting point
4 Use a threshold pixel level based upon the pointed to inside and outside pixel levels
5 Scan along the x axis until the first pixel equal to or less than the threshold level is found
6 Use the x coordinate of the found pixel as the right and left edge x coordinate
7 Compute the mean x coordinate
8 Scan along the y axis until the first pixel equal to or less than the threshold level is found
9 Use the y coordinate of the found pixel as the top and bottom edge y coordinate
10 Compute the mean y coordinate
11 Use computed mean x,y coordinate as the center of reference mark Improvements being tested:

Method Two Improvement:

Instead of using the coordinate of the pixel equal to or less than the threshold level, use the interpolated factional coordinate:

Left Coordinate=x coordinate+((pixel x+1 level)−threshold)/((pixel x+1 level)−(pixel x level))
Right Coordinate=x coordinate−((pixel x level)−threshold)/((pixel x level)−(pixel x−1 level))
Top Coordinate=y coordinate+((pixel y+1 level)−threshold)/((pixel y+1 level)−(pixel y level))
Bottom Coordinate=y coordinate−((pixel y level)−threshold)/((pixel y level)−(pixel y−1 level))

This improvement changes method two resolution to much better than its previous one half pixel.

Improved Estimation of Center of Reference Mark:

Using either method one or two locate the approximate center of the reference mark. Use the first found value of the center as the starting point of a second approximation of the center.

This improvement changes the reproducibility of the found center to better than one tenth of a pixel.

Positioning by Method of Successive Approximation:

Step Description
1 Use one of the previously disclosed methods of finding the centers
2 Compute the angle error and center of rotation of the image
3 Adjust the image to an approximate standard position and rotation
4 Find the new centers of the reference marks using the same find method
5 Compute the new angle error and center of rotation
6 If the new angle error and center of rotation are too large go to step 3

This improvement changes the reproducibility of the rotation and position of the image to better than five hundredths of a degree and one pixel.

This method can be performed using the current software. However, it requires repeated operator interaction and a substantial amount of time for the repeated adjustment to standard position and rotation.

Step Description
1 Find the centers of the reference marks by either improved method
2 Use the right, left, top, and bottom coordinates to determine the size of the reference mark
3 Use the same method used in the measure image feature to create the pixel pattern across the reference marks as follows:
   a: The diameter plus a small amount through the center parallel to the line between centers
   b: The diameter plus a small amount through the center perpendicular to the line between centers
4 Determine the maximum and minimum pixel level in the pixel patterns
5 Compute the edge coordinates of the half way level in each pattern
6 Use the mean coordinates as the center coordinates for step 3 until the difference between the new center and the previously found center is less than a to be specified fraction of a pixel
7 Use the final found centers as a basis for adjusting the digital image to standard position and rotation This method has the advantage of requiring only one sequence of operator actions and only one adjustment to standard position and rotation.

Review of the Measure Image Pixel Pattern:

Step Description
1. Determine two different position coordinates on the image
2. Compute the equation of the line between the two coordinates
3. Compute the image coordinates of one pixel increments along that line
4. Determine the pixel value at each pixel pattern coordinate
   a: The pixel pattern coordinates may be fractional coordinates
   b: The image pixels are at integral coordinates
   c: The pixel value will be determined by the same method used by the rotate-translate routine—an opposing area weighted mean of the nearest four pixel values Although the present invention and its advantages have been described in detail, it should be understood that various changes, substitutions and alterations can be made herein without departing from the spirit and scope of the invention. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the invention is intended to include within its scope such processes, machines, manufacture, compositions of matter, means, methods, or steps.

The invention claimed is:

1. A digitized tomosynthesis method for obtaining information about the internal structure of an object and displaying the information as a 3D volumetric image, comprising:
   directing a ray of energy from a source to and through the object to directly impinge on an energy sensor defining an image plane;
   tilting and rotating the object, but not the energy source, about an axis of rotation at a canted angle with respect to the image plane;
   thereby enabling information representative of the internal structure of the object to be acquired by the energy sensor at successive rotational positions of the object; and
   forming and displaying said information as said 3D volumetric image.

2. The method of claim 1 in which the energy is in the form of electromagnetic radiation.

3. The method of claim 2 in which the electromagnetic radiation is x-ray radiation.

4. The method of claim 1 in which the energy sensor is a flat panel digital detector.

5. The method of claim 1 in which an optical axis of the source is perpendicular to the image plane.

6. The method of claim 1 in which a ray of energy from the source is mathematically traced through a voxel of an object space to the image plane, a coordinate of a shadow of the voxel on the image plane is computed for each object rotation, and image data is extracted and combined to form the object space voxel.

7. A digitized tomosynthesis method for obtaining information about the internal structure of an object and displaying the information as a 3D volumetric image, comprising:
   directing a ray of energy from a source to and through the object to directly impinge on an energy sensor defining an image plane;
   rotating the object, but not the energy source, about an axis of rotation at a canted angle with respect to the image plane thereby enabling information representative of the internal structure of the object to be acquired by the energy sensor at successive rotational positions of the object;
   determining the source and object angles relative to the energy sensor by:
   determining the axis of rotation of the object;
   placing a first registration marker that is substantially opaque to the energy on a first location proximate the sensor and along the object's axis of rotation;
   obtaining a first shadow image corresponding to the first registration marker by exposing the first registration marker to energy from the energy source;
   placing a second registration marker that is substantially opaque to energy levels at a location distal from the sensor, spaced a predetermined distance from said first location along the object's axis of rotation;
   obtaining a second shadow image corresponding to the second registration marker by exposing the second registration marker to energy from the energy source;
   comparing a location of the first shadow image and a location of the second shadow image to determine the source and object angles relative to the energy sensor; and
   forming and displaying said information as said 3D volumetric image.

8. The method of claim 7 wherein the first registration marker and the second registration marker are the same marker.

9. The method of claim 8 wherein the second registration marker is supported at the predetermined distance by a pedestal.

10. The method of claim 9 wherein the pedestal is substantially transparent to said ray of energy.

11. The method of claim 7 wherein an orientation between the energy source and a sensor surface comprises information including at least one of an angle of misalignment and an angle of inclination of the rotational axis of the object.

12. The method of claim 11 wherein the orientation between the energy source and the sensor surface comprises both the angle of misalignment and the angle of inclination of the rotational axis of the object.

13. The method of claim 7 further comprising the steps of:
   positioning an object proximate a surface of the energy sensor;
   obtaining one or more object shadow images with the energy sensor by exposing the object to energy from the energy source; and
   manipulating the one or more object shadow images as a function of an orientation between the energy source and the sensor surface.

14. The method of claim 13 further comprising the steps of:
   rotating at least one of the energy source and the object about a center of rotation to a plurality of rotational positions;
   obtaining an object shadow image at each of the plurality of rotational positions by exposing the object to energy from the energy source at each of the plurality of rotational positions;
   combining object shadow images obtained at the plurality of rotational positions to obtain a three-dimensional image of the object; and manipulating the three-dimensional image of the object as a function of the orientation between the energy source, the rotational axis of the object, and the sensor surface.

15. In a digitized tomosynthesis system for obtaining a 3D volumetric image of an object in which a ray of energy from a source travels through the object to directly impinge on an energy sensor defining an image plane and in which an axis of rotation at a canted angle with respect to the image plane is provided, and the object, but not the energy source, is rotated about an axis whereby an image is acquired by the energy sensor at successive rotational positions of the object, the improvement according to which the system includes a support for the object enabling the object to be tilted and rotated about an axis of rotation, the axis of rotation of the object being at a canted angle with respect to the image plane.

16. The system of claim 15 in which the energy is in the form of electromagnetic radiation.

17. The system of claim 16 in which the electromagnetic radiation is x-ray radiation.

18. The system of claim 15 in which the energy sensor is a flat panel digital detector.

19. The system of claim 15 in which an optical axis of the source is perpendicular to the image plane.

20. The system of claim 15 including a computer chip containing one or more computer programs for enabling a ray of energy from the source to be mathematically traced through a voxel of an object space to the image plane, for computing a coordinate of a shadow of the voxel on the image plane for each object rotation, and for extracting image data, and for combining the extracted image data to form the object space voxel.

21. In a digitized tomosynthesis system for obtaining a 3D volumetric image of an object in which a ray of energy from a source travels through the object to impinge on an energy sensor defining an image plane and in which an axis of rotation at a canted angle with respect to the image plane is provided, and the object is rotated about an axis whereby an image is acquired by the energy sensor at successive rotational positions of the object, the improvement according to which the system includes a support for the object enabling the object to be rotated about an axis of rotation at a canted angle with respect to the image plane, the system including a computer chip containing one or more computer programs for enabling a ray of energy from the source to be mathematically traced through a voxel of an object space to the image plane, for computing a coordinate of a shadow of the voxel on the image plane for each object rotation, and for extracting image data, and for combining the extracted image data to form the object space voxel, and enabling the source and object angles to be determined relative to the energy sensor by further comprising:

at least one mechanism for determining the axis of rotation of the object;

a first registration marker that is substantially opaque to the energy disposed on a first location proximate the sensor and along the object's axis of rotation whereby to enable a first shadow image corresponding to the first registration marker to be obtained when the first registration marker is exposed to energy from the energy source; and a second registration marker that is substantially opaque to energy levels disposed at a location distal from the sensor, spaced a predetermined distance from said first location along the object's axis of rotation whereby to enable a second shadow image corresponding to the second registration marker to be obtained by exposing the second registration marker to energy from the energy source;

said one or more computer programs being capable of comparing a location of the first shadow image and a location of the second shadow image to determine the source and object angles relative to the energy sensor.

22. The system of claim 21 wherein the first registration marker and the second registration marker are the same marker.

23. The system of claim 22 wherein the second registration marker is supported at the predetermined distance by a pedestal.

24. The system of claim 23 wherein the pedestal is substantially transparent to said ray of energy.

25. The system of claim 21 wherein an orientation between the energy source and a sensor surface comprises information including at least one of an angle of misalignment and an angle of inclination of the rotational axis of the object.

26. The system of claim 25 wherein the orientation between the energy source and the sensor surface comprises both the angle of misalignment and the angle of inclination of the rotational axis of the object.

27. The system of claim 21 further comprising: an object positioned proximate a surface of the energy sensor; and a mechanism for obtaining one or more object shadow images with the energy sensor by exposing the object to energy from the energy source; said one or more computer programs being capable of manipulating the one or more object shadow images as a function of an orientation between the energy source and the sensor surface.

28. The system of claim 27 further comprising a mechanism for rotating at least one of the energy source and the object about a center of rotation to a plurality of rotational positions, and obtaining an object shadow image at each of the plurality of rotational positions by exposing the object to energy from the energy source at each of the plurality of rotational positions; and said one or more computer programs being capable of combining object shadow images obtained at the plurality of rotational positions to obtain a three-dimensional image of the object, and manipulating the three dimensional image of the object as a function of the orientation between the energy source, the rotational axis of the object, and the sensor surface.

29. An apparatus for representing an internal structure of an object by digitized tomosynthesis in which a ray of energy from a source travels through an object to directly impinge on an energy sensor defining an image plane and in which an axis of rotation at a canted angle with respect to the image plane is provided, and the object is rotated about an axis, but not the energy source, whereby a 3D volumetric image of an object is acquired by the energy sensor at successive rotational positions of the object, the improvement according to which the apparatus includes a support for the object enabling the object to be tilted and rotated about an axis of rotation, the axis of rotation of the object being at a canted angle with respect to the image plane.

30. The apparatus of claim 29 in which the energy is in the form of electromagnetic radiation.

31. The apparatus of claim 30 in which the electromagnetic radiation is x-ray radiation.

32. The apparatus of claim 29 in which the energy sensor is a flat panel digital detector.

33. The apparatus of claim 29 in which an optical axis of the source is perpendicular to the image plane.

34. The apparatus of claim 29 including a computer chip containing one or more computer programs for enabling a ray of energy from the source to be mathematically traced through a voxel of an object space to the image plane, for computing a coordinate of a shadow of the voxel on the image plane for each object rotation, and for extracting image data, and for combining the extracted image data to form the object space voxel.

35. An apparatus for representing an internal structure of an object by digitized tomosynthesis in which a ray of energy from a source travels through an object to impinge on an energy sensor defining an image plane and in which the object is rotated about an axis whereby a 3D volumetric image of an object is acquired by the energy sensor at successive rotational positions of the object, the improvement according to which the apparatus includes a support for the object enabling the object to be rotated about an axis of rotation at a canted angle with respect to the image plane, the apparatus including a computer chip containing one or more computer programs for enabling a ray of energy from the source to be mathematically traced through a voxel of an object space to the image plane, for computing a coordinate of a shadow of the voxel on the image plane for each object rotation, and for extracting image data, and for combining the extracted image data to form the object space voxel and enabling the source and object angles to be determined relative to the energy sensor, the apparatus further comprising:

at least one mechanism for determining the axis of rotation of the object; a first registration marker that is substantially opaque to the energy disposed on a first location proximate the sensor and along the object's axis of rotation whereby to enable a first shadow image corresponding to the first registration marker to be obtained when the first registration marker is exposed to energy from the energy source; and a second registration marker that is substantially opaque to energy levels disposed at a location distal from the sensor, spaced a predetermined distance from said first location along the object's axis of rotation whereby to enable a second shadow image corresponding to the second registration marker to be obtained by exposing the second registration marker to energy from the energy source;

said one or more computer programs being capable of comparing a location of the first shadow image and a location of the second shadow image to determine the source and object angles relative to the energy sensor.

36. The apparatus of claim 35 wherein the first registration marker and the second registration marker are the same marker.

37. The apparatus of claim 36 wherein the second registration marker is supported at the predetermined distance by a pedestal.

38. The apparatus of claim 37 wherein the pedestal is substantially transparent to said ray of energy.

39. The apparatus of claim 35 wherein an orientation between the energy source and a sensor surface comprises information including at least one of an angle of misalignment and an angle of inclination of the rotational axis of the object.

40. The apparatus of claim 39 wherein the orientation between the energy source and the sensor surface comprises both the angle of misalignment and the angle of inclination of the rotational axis of the object.

41. The apparatus of claim 35 further comprising: an object positioned proximate a surface of the energy sensor; and a mechanism for obtaining one or more object shadow images with the energy sensor by exposing the object to energy from the energy source; said one or more computer programs being capable of manipulating the one or more object shadow images as a function of an orientation between the energy source and the sensor surface.

42. The apparatus of claim 41 further comprising a mechanism for rotating at least one of the energy source and the object about a center of rotation to a plurality of rotational positions, and obtaining an object shadow image at each of the plurality of rotational positions by exposing the object to energy from the energy source at each of the plurality of rotational positions; and said one or more computer programs being capable of combining object shadow images obtained at the plurality of rotational positions to obtain a three-dimensional image of the object, and manipulating the three-dimensional image of the object as a function of the orientation between the energy source, the rotational axis of the object, and the sensor surface.

* * * * *